United States Patent [19]

Aslam et al.

[11] Patent Number: 5,151,540

[45] Date of Patent: Sep. 29, 1992

[54] THIO CARBAMATES AND THEIR DERIVATIVES

[75] Inventors: Mohammad Aslam; Kenneth G. Davenport, both of Corpus Christi, Tex.

[73] Assignee: Hoechst Celanese Corporation, Somerville, N.J.

[21] Appl. No.: 935,461

[22] Filed: Nov. 26, 1986

[51] Int. Cl.$^5$ .................. C07C 333/00; C07C 211/00
[52] U.S. Cl. ..................... 558/232; 558/242; 558/234; 558/241; 564/428
[58] Field of Search ............ 558/242, 232, 234, 241; 564/428

[56] References Cited

U.S. PATENT DOCUMENTS 3,476,791 11/1969 Newman et al. ............. 558/234
4,524,217 6/1985 Davenport et al. ........... 564/223

OTHER PUBLICATIONS

Reid, Org. Chem. of BiValent Sulfur, vol. IV, p. 201, Chem. Pub. Co., Inc., N.Y., 1962.
Chem. Ber., vol. 58, 1925, pp. 36–51.
Synthetic Communications, 12 (11), 941–944 (1983).
Pearson, et al., J. Am. Chem. Soc., 1953, pp. 5905–5908.
Newman, et al., J. Org. Chemistry, vol. 31, pp. 3980–3984 (1966).
Kwart, et al., J. Org. Chemistry, vol. 31, pp. 410–413 (1966).

*Primary Examiner*—M. Lee
*Assistant Examiner*—Robert C. Whittenbaugh
*Attorney, Agent, or Firm*—Marvin Turken; Donald R. Cassady

[57] ABSTRACT

A method is provided for preparing N-acylaminothiophenols, e.g., N-acetyl-para-aminothiophenol, or aminothiophenols, e.g., para-aminothiophenol, or N,S-diacylaminothiophenols, e.g., N,S-diacetyl-para-aminothiophenol, by reacting any of certain sulfur-containing ketones, viz., an S-(acylaryl) N,N-di(organo)thiocarbamate, e.g., S-(4'-acetophenyl)-N,N-dimethylthiocarbamate, an acylthiophenol acylate ester, e.g., 4-acetothiophenol acetate, or a free acylthiophenol, e.g., 4-acetothiophenol with hydroxylamine or a hydroxylamine salt, to form the oxime of the ketone, subjecting the oxime to a Beckmann rearrangement in the presence of a catalyst to form an S-(N-acyl-aminoaryl) N,N-di(organo)thiocarbamate, e.g., S-(N-acetyl-para-aminophenyl) N,N-dimethylthiocarbamate, an N,S-diacylaminothiophenol, e.g., N,S-diacetyl-paraaminothiophenol, or an N-acyl aminothiophenol, e.g., N-acetyl-para-aminothiophenol, respectively. The S-(N-acyl-aminoaryl) N,N-di(organo)thiocarbamate may be hydrolyzed to the N-acyl aminothiophenol or aminothiophenol. The S-(acylaryl) N,N-di(organo)thiocarbamate may be produced by reacting a hydroxy aromatic ketone, e.g., 4-hydroxyacetophenone (4-HAP) with an N,N-di(organo)thiocarbamoyl halide, e.g., N,N-dimethylthiocarbamoyl chloride (DMTC) to form an O-(acylaryl) N,N-di(organo)thiocarbamate, e.g., O-(4'-acetophenyl) N,N-dimethylthiocarbamate, and pyrolytically rearranging the latter compound. The acylthiophenol may be produced by hydrolyzing the S-(acylaryl) N,N-di(organo)-thiocarbamate.

6 Claims, No Drawings

THIO CARBAMATES AND THEIR DERIVATIVES

BACKGROUND OF THE INVENTION

This invention relates to the production of aminothiophenols, e.g., para-aminothiophenol, and their derivatives, such as N-acyl-aminothiophenols, e.g., N-acetyl-para-aminothiophenol.

Aminothiophenols and their derivatives have various actual and potential uses in commerce. For example, aminothiophenols such as para-aminothiophenol are important intermediates for the synthesis of pharmaceuticals such as antiarthritics, steroid derivatives, and anti-malarials, and are also used as photograph antifogging agents.

U.S. Pat. No. 4,524,217, issued Jun. 18, 1985 to K. G. Davenport and C. B. Hilton, and assigned to the same assignee as this application, teaches the preparation of N-acyl-hydroxy aromatic amines, e.g., N-acetyl-paraaminophenol (APAP), by reacting a hydroxy aromatic ketone, e.g., 4-hydroxyacetophenone (4-HAP), with hydroxylamine or a hydroxylamine salt, to form the oxime of the ketone, and subjecting the oxime to a Beckmann rearrangement in the presence of a catalyst to form the N-acyl-hydroxy aromatic amine. The patent also discloses the preparation of hydroxy aromatic esters such as phenyl acetate or the Friedel-Crafts acylation of phenols using hydrogen fluoride as catalyst and cites several references disclosing these reactions. The entire disclosure of this patent is incorporated by reference.

Auwers et al, Chemische Berichte 58, 36-51 (1925), show the Beckmann rearrangement of a large number of oximes of aromatic ketones, most of which are substituted acetophenones.

Ganboa et al, Synthetic Communications 13, 941-944 (1983), show the production of acetanilide from acetophenone by refluxing in a solution of hydroxylamine hydrochloride.

None of the three preceding references discloses any method for the preparation of an N-acyl aromatic amine from an aromatic ketone by oxime formation and Beckmann rearrangement, where the aromatic groups have a sulfur-containing ring substituent such as mercapto or thiocarbamoyl.

Newman et al, Journal of Organic Chemistry 31, 3980-3984 (1966), teach the formation of O-aryl dialkylthiocarbamates by reaction of a phenol with a dialkyl thiocarbamoyl chloride, and the pyrolytic rearrangement of O-aryl dialkylthiocarbamates to S-aryl dialkylthiocarbamates. Specifically disclosed in Table I is the pyrolytic rearrangement of O-4-acetophenyl to S-4-acetophenyl dimethylthiocarbamate.

Newman et al, U.S. Pat. No. 3,476,791, disclose a process similar to that disclosed in the article cited in the preceding paragraph and was issued to patentees who are the same as the authors of such article. Example 14 of the patent shows the preparation of p-acetylphenyl dimethylthiolcarbamate from p-acetylphenyl dimethylthioncarbamate.

Kwart et al, Journal of Organic Chemistry, 31, 410-413 (1966), show the vapor phase pyrolytic rearrangement of various diaryl thioncarbonates to O,S-diaryl thiolcarbonates and of various O-aryl dialkylthioncarbamates to S-aryl dialkylthiolcarbaeates.

Copending application Ser. No. 875,158 filed Jun. 17, 1986 by Davenport and assigned to the same assignee as this application discloses a method of producing aminothiophenols and their derivatives, including a somewhat different sequence of reactions than that of the instant application.

SUMMARY OF THE INVENTION

In accordance with this invention, aminothiophenols, and their derivatives such as N-acyl-aminothio-phenols, or N,S-diacylaminothio-phenols, are produced by subjecting any of certain sulfur-containing ketones, viz., an acylthiophenol, either unmodified, or, preferably with the thiol group masked, i.e., esterified, with a thiocarbamoyl or acyl group, to reaction with hydroxylamine or a hydroxylamine salt, to form the oxime of the ketone, and subjecting the oxime to a Beckmann rearrangement in the presence of a catalyst to form the free N-acylaminothiophenol or its corresponding thioester. The latter compounds may be hydrolyzed to obtain an N-acyl aminothiophenol (in the case of thioesters), or an aminothiophenol. The N-acyl-aminothiophenol may be reacted with an acylating agent to form an N,S-diacylaminothiophenol, or may be hydrolyzed to the aminothiophenol.

The reaction of the sulfur-containing ketone with hydroxylamine added as is or from a hydroxylamine salt to form the oxime of the ketone proceeds as shown in equation (I):

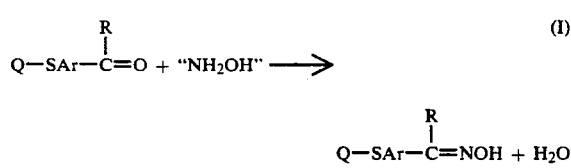

where Ar is a divalent aromatic radical, Q is H,

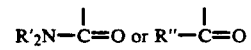

and R, R' and R" are monovalent organo radicals as further defined hereinafter. R, R' and R" when used in the naming of organic compounds herewithin are called "organo".

The Beckmann rearrangement of the latter oxime to form an N-acyl-aminothiophenol or its thioester proceeds as in equation (II):

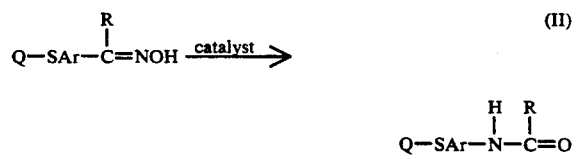

When Q is

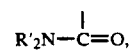

the hydrolysis of the resulting S-(N-acyl-aminoaryl) N,N-di(organo)thiocarbamate produced as in equation (II) forms the N-acyl aminothiophenol as shown in equation (III):

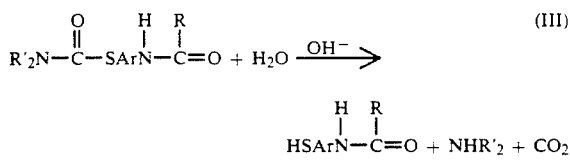

(III)

Under more stringent hydrolysis conditions, the hydrolysis results in the formation of the free aminothiophenol as shown in equation (IV):

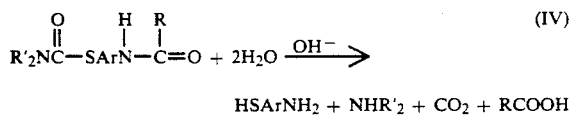

(IV)

The acylation of the thiol group of the N-acyl aminothiophenol proceeds as in equation (V):

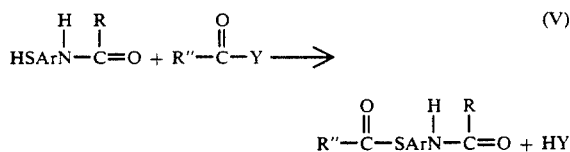

(V)

where Y is the residue of an acylating agent and R'' is a monovalent organo radical as more fully defined hereinafter.

The N-acyl aminothiophenol produced by the Beckmann rearrangement of equation (II) or by hydrolysis as in equation (III) may be further hydrolyzed to the aminothiophenol as shown in equation (VI):

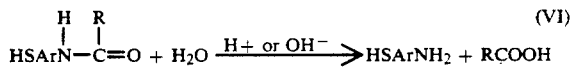

(VI)

The sulfur-containing ketone starting compounds of equation (I) may be produced by any method known in the art. It is preferable, however, that an S-(acylaryl) N,N-di(organo)thiocarbamate be initially produced by reacting a hydroxy aromatic ketone, e.g., 4-hydroxyacetophenone (4-HAP) with an N,N-di(organo)thiocarbamoyl halide, e.g., N,N-dimethylthiocarbamoyl chloride (DMTC) to form an O-(acylaryl) N,N-di(organo)thiocarbamate, e.g., O-(4'-acetophenyl) N,N-dimethylthiocarbamate, and pyrolytically rearranging the O-(acylaryl) N,N-di(organo)thiocarbamate to form an S-(acylaryl) N,N-di(organo)thiocarbamate, e.g., S-(4'-acetophenyl) N,N-dimethylthiocarbamate. The latter compound may be transformed directly into desired products by means of the reactions shown in foregoing equations (I) to (VI). Alternatively, such compound may be hydrolyzed to an acylthiophenol as shown in equation (IX) hereinafter, wherein the acyl group is bonded to a ring carbon atom, and the acylthiophenol may be formed into the same products by the reactions of equations (I), (II), (V) and (VI). Preferably, however, the thiol group of the acylthiophenol is first protected against further reaction. Such protection can be accomplished by acylation, e.g., with an acylating agent such as an acyl halide or alkanoic acid anhydride, in accordance with equation (X) shown hereinafter before being subsequently reacted as shown in equations (I) and (II) to form the N,S-diacylaminothio-phenol.

The reaction between a hydroxy aromatic ketone and an N,N-di(organo)thiocarbamoyl halide to form an O-(acylaryl) N,N-di(organo)thiocarbamate is as shown in equation (VII):

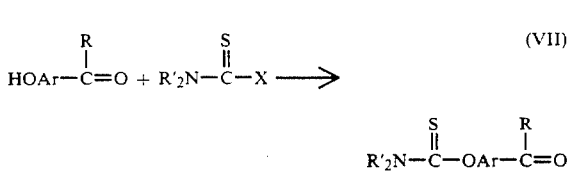

(VII)

where X is halide, e.g., chloride, bromide, or iodide, and Ar, R and R' are used as in equation (I).

The pyrolytic rearrangement of the O-(acylaryl) N,N-di(organo)thiocarbamate to the S-(acylaryl) N,N-di(organo)thiocarbamate proceeds as in equation (VIII):

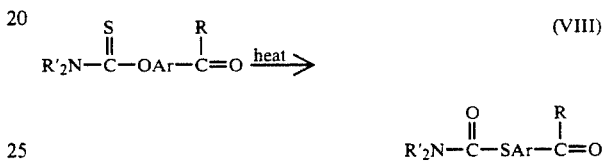

(VIII)

The hydrolysis of an S-(acylaryl) N,N-di(organo)thiocarbamate to an acylthiophenol proceeds as in equation (IX):

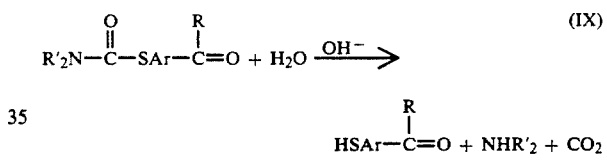

(IX)

The acylation of the thiol group of the acylthiophenol proceeds as in equation (X):

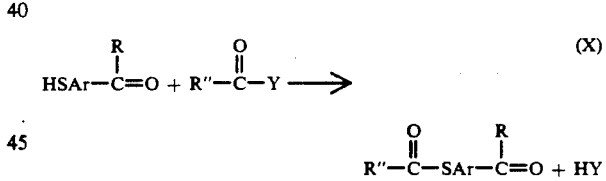

(X)

In the foregoing equations Ar is a divalent aromatic radical. The specific nature of the radical is not critical but it is preferably a radical resulting from the removal of two ring hydrogen atoms from benzene or naphthalene, either unsubstituted or with ring hydrogens substituted with radicals such as alkyl, alkenyl, alkynyl, alkoxy or acyloxy containing 1 to 18 carbon atoms, aralkyl containing 7 to 18 carbon atoms; halogen, e.g. chlorine, bromine, or iodine; hydroxy or acyloxy; and amino or acylamido. Ar is preferably 1,4-phenylene or 2,6-naphthylene, and most preferably 1,4-phenylene.

R and R'' in the foregoing equations may be the same or different and are each a radical containing, for example, 1 to 18 carbon atoms preferably 1 to 4 carbon atoms. R and R'' may be, for example, alkyl, alkenyl, alkynyl, alkoxyalkyl acylalkyl, or acyloxyalkyl containing 1 to 18 carbon atoms, either unsubstituted or substituted with radicals such as halogen, e.g., chlorine, bromine, or iodine; hydroxy or acyloxy; amino or acylamido; or an aryl radical, which may be a monovalent radical corresponding to the definition of Ar given above except that only one ring hydrogen is removed to form the open valence attached to the R moiety. More preferably, R and R" are each methyl, ethyl, propyl, or n-butyl and most preferably methyl.

The amine organo groups of the contemplated thiocarbamates, i.e., R' in equations (I) to (IV) and (VII) to (IX) are such that the amine nitrogen atom is attached to two different carbon atoms each of which is saturated with hydrogen atoms, other carbon atoms or a combination of those, or is an aromatic ring carbon atom. The organo groups may be, for example, any of the groups identified by Newman et al, as satisfying $R_4$ and $R_5$ in Formula V shown in their U.S. Pat. No. 3,476,791, the entire disclosure of which is incorporated by reference, or such organo groups may be any of those identified previously as satisfying R and R" in equations (I) to (X) herein. Preferably, R' is lower alkyl, e.g., containing 1 to 4 carbon atoms such as methyl, ethyl, propyl, or n-butyl and is most preferably methyl.

In equations (V) and (X), Y is the residue minus the acyl group,

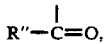

of compounds which are known acylating agents, such as hydroxy, acyloxy, e.g., acetoxy, and halide, e.g., fluoride, chloride, and bromide. Acylating agents which may be used are, for example, alkanoic acids, preferably $C_2$-$C_5$ alkanoic acids, e.g., acetic and propionic acids, alkanoic acid anhydrides, preferably $C_2$ to $C_5$ alkanoic acid anhydrides, e.g., acetic and propionic anhydrides, and acyl halides, preferably $C_2$ to $C_5$ acyl halides, e.g., acetyl and propionyl fluorides, chlorides, and bromides.

Preferably, the process of the invention is carried out such that, in the foregoing equations, Ar is 1,4-phenylene, R, R' and R" are methyl, and X and Y are chloride, such that, for example 4-hydroxyacetophenone (4-HAP) is reacted with N,N-dimethylthiocarbamoyl chloride (DMTC) to form O-(4'-acetophenyl) N,N-dimethyl thiocarbamate (equation VII), which in turn is pyrolytically rearranged to form S-(4'-acetophenyl)-N,N-dimethylthiocarbamate (equation VIII). The latter is then reacted with hydroxylamine or a hydroxylamine salt, to form the oxime (equation I) which is then subjected to a Beckmann rearrangement to form S-(N-acetyl-p-aminophenyl) -N,N-dimethylthiocarbamate (equation II), which may then be hydrolyzed to N-acetyl-para-aminothiophenol (equation III), or p-aminothiophenol (equation IV). The former compound may then be acetylated, e.g., with acetic anhydride, to form N,S-diacetyl-p-aminothiophenol (equation V), or may be further hydrolyzed to form para-aminothiophenol (equation VI).

Preferably, the hydroxy aromatic ketone, e.g., 4-HAP, used as the starting compound for the reaction of equation (VII) is prepared by the Fries rearrangement of an aromatic ester, e.g., phenyl acetate, or the Friedel-Crafts acylation of a phenolic compound, e.g., phenol, with an acylating agent, e.g., acetic acid or acetic anhydride, using hydrogen fluoride as catalyst, since this allows for the production of the N-acyl-aminothiophenol starting with relatively cheap and available raw materials. Conditions for these reactions are shown in the previously cited U.S. Pat. No. 4,524,217, the disclosure of which has been incorporated herein by reference. If 4-HAP is used as an intermediate in obtaining the desired product, the procedures for producing 4-HAP from phenol and acetic acid or anhydride may be used which are disclosed in pending U.S. patent applications, Ser. No. 714,407, filed Mar. 21, 1985 by Davenport et al, Ser. No. 716,016, filed Mar. 26, 1985 by Mott et al, and Ser. No. 721,007, filed Apr. 8, 1985 by Mott, now U.S. Pat. No. 4,607,125. issued Aug. 19, 1986, the entire disclosures of which are incorporated by reference. Similarly, if 6-hydroxy-2-acetonaphthone (6,2-HAN) is used as an intermediate, procedures for producing this product by the Friedel-Crafts acylation of 2-naphthol with acetic anhydride or acetic acid, and by the Fries rearrangement of 2-naphthyl acetate are shown respectively in U.S. Pat. No. 4,593,125, issued Jun. 3, 1986 to Davenport et al, and pending application Ser. No. 870,062, filed Jun. 3, 1986 by Davenport. The entire disclosures of the foregoing patent and application are incorporated by reference.

The formation of O-(acylaryl) N,N-di(organo) thiocarbamate indicated by equation (VII) may be accomplished by contacting the hydroxy aromatic ketone, e.g., 4-HAP, with the N,N-di(organo)thiocarbamoyl halide, e.g., DMTC, at a temperature of about 25° to 50° C. for a period of about 30 to 60 minutes. Preferably the reaction is carried out in the presence of a base, e.g., sodium hydroxide, potassium hydroxide, sodium hydride or sodium methoxide. The reaction may be carried out in the presence of an appropriate solvent, e.g., one which is capable of dissolving at least part of the reactants and is inert to the reaction. Solvents which can be used are dimethyl formamide, and alcohols, e.g., methanol, ethanol and t-butanol.

The pyrolytic rearrangement of the foregoing O-aryl thiocarbamate to the S-(acylaryl) N,N-di(organo) thiocarbamate (equation VIII) may be accomplished by heating the O-aryl thiocarbamate to a temperature of about 200° to 300° C. for a period of about 30 to 120 minutes. In general, the lower the temperature, the longer the period of time to effect substantially complete rearrangement of the O-aryl to the S-aryl thiocarbamate.

The conversion of a sulfur-containing aromatic ketone, e.g., S-(acylaryl) N,N-di(organo)thiocarbamate or acylthiophenol, into its oxime as indicated by equation (I), is accomplished by contacting the ketone with hydroxylamine or a hydroxylamine salt, e.g. hydroxylamine hydrochloride, hydroxylamine sulfate, hydroxylamine bisulfate, or hydroxylamine phosphate, and a base if a hydroxylamine salt is employed, e.g., ammonium hydroxide, potassium hydroxide, sodium hydroxide, or lithium hydroxide in an amount, for example of about 1.0 to 2.0 moles per mole of hydroxylamine salt, at a temperature, for example of about 50° to 100° C. for a period, for example, of about 1 to 4 hours. Any pressure may be used, e.g., about 80 mm of mercury to about 10 atmospheres absolute. The reaction is preferably carried out in an aqueous or alcoholic medium, i.e., in the presence of water and/or an alcohol such as methanol, ethanol, or isopropanol.

The oxime is converted into the corresponding N-acyl amino compound by a Beckmann rearrangement as shown in equation (II), by contacting the oxime with a catalyst for the reaction at a temperature, for example, of about 0° C. to about the refluxing temperature of the reaction liquid for a period of about 1 to 4 hours. The pressure is not critical and may be, for example, in the range of about 80 mm of mercury to 10 atmospheres absolute. Any Beckmann rearrangement catalyst may be used, as for example, an acid, e.g., a mineral acid such as sulfuric, hydrochloric or a phosphoric acid, e.g. a polyphosphoric acid, an organic acid such as trifluoroacetic acid, para-toluenesulfonic acid, benzenesulfonic acid or methanesulfonic acid, an acidic ion-exchange resin such as Amberlyst 15 or Nafion 501 which are sulfonic acid ion-exchange resins, or thionyl chloride in nitromethane or liquid sulfur dioxide.

The hydrolysis reactions shown in equations (III), (IV), and (IX) may be accomplished by heating the compound and a base, e.g., sodium or potassium hydroxide or an alkyl amine, in an aqueous glycol or alcohol, e.g., methanol, ethanol or t-butanol solution in an inert atmosphere of, e.g., nitrogen, under reflux conditions. For example, to obtain an N-acyl aminothiophenol as shown in equation (III) a solution of about 0.5 to 2M concentration of S-(acylaryl) thiocarbamate and about 1 to 4M concentration of a base such as potassium or sodium hydroxide in aqueous ethylene glycol, or alcohol, e.g., containing about 25 to 50 wt. % of water, may be refluxed for about 1 to 4 hours. To obtain the free aminothiophenol as shown in equation (IV), a solution of S-(acylaryl) thiocarbamate, e.g., about 2 to 8M concentration in the same base solution may be refluxed for a longer period, e.g., about 4 to 8 hours.

The acylation of the N-acyl aminothiophenol to obtain the N,S-diacyl aminothiophenol as shown in equation (V) may be carried out, for example, by contacting the former compound with about 1 to 10 moles of an acylation agent such as acetic anhydride, per mole of N-acyl aminothiophenol at a temperature of about 20° to 140° C. for a period of about 15 to 120 minutes either in the absence or presence of base, e.g., potassium hydroxide, sodium acetate, or organic bases such as pyridine or triethylamine.

DESCRIPTION OF SPECIFIC EMBODIMENTS

The following examples further illustrate the invention.

Example 1 illustrates the formation of O-(4'-acetophenyl) N,N-dimethylthiocarbamate by reaction of 4-hydroxyacetophenone with N,N-dimethylthiocarbamoyl chloride (DMTC) in accordance with equation (VII) wherein Ar is 1,4-phenylene, and R and R' are methyl.

EXAMPLE 1

A 5 liter flask equipped with a mechanical stirrer was charged with KOH (123.2 g, 2.2 mol) and methanol (500 mL). The solution was cooled in ice, 4-hydroxyacetophenone (272 g, 2.0 mol) added and the reaction mixture stirred for 0.25 h. N,N-Dimethylthiocarbamoyl chloride (274 g, 2.2 mol) was added and the reaction mixture gradually warmed to room temperature. An exothermic reaction was observed and a solid precipitated. After stirring the reaction mixture for an additional 0.5 h, water (3 L) was added. The contents of the flask were cooled in ice and the ensuing precipitate was collected via filtration and washed with water. Drying of the solid in vacuo (150 mm HgA) at 50° C. afforded 382 g (85.7 % yield) of O-(4'acetophenyl) N,N-dimethylthiocarbamate. The product was 97 % pure by high performance liquid chromatography (HPLC).

Example 2 illustrates the formation of S-(4'-acetophenyl) N,N-dimethylthiocarbamate by the pyrolytic rearrangement of O-(4'-acetophenyl) N,N-dimethylthiocarbamate in accordance with equation (VIII) where Ar is 1,4-phenylene and R and R' are methyl.

EXAMPLE 2

O-(4,-acetophenyl) N,N-dimethylthiocarbamate (300 g, 1.35 mol) was heated under an inert atmosphere at 220° C. for 1 h. A water:methanol mixture (5:1, 600 mL) was added with stirring while the flask was hot causing a yellow solid to precipitate. The solid was filtered and washed with water. Drying of the solid in vacuo (150 mm HgA) at 50° C. afforded S-(4'acetophenyl) N,N-dimethylthiocarbamate (291.5 g, 97.2% yield). HPLC analysis showed complete conversion to the product.

Example 3 illustrates the formation of the oxime of S-(4'-acetophenyl) N,N-dimethylthiocarbamate in accordance with equation (I) where Ar is 1,4-phenylene and R and R' are methyl.

EXAMPLE 3

A solution of S-(4'-acetophenyl) N,N-dimethylthiocarbamate (22.3 g, 0.1 mol) and hydroxylamine sulfate (32.4 g, 0.2 mol) in ethanol:water (1:2, 150 mL) was heated to 75° C. and ammonium hydroxide (17M, 6 mL) was added. The reaction mixture was heated to reflux for 1 h and gradually cooled to room temperature. A yellow solid precipitated, which was collected via filtration and washed with water. The solid was dried in vacuo (150 mm HgA) at 50° C. to afford the oxime of S-(4'-acetophenyl) N,N-dimethylthiocarbamate. The product was recrystallized with 95% ethanol. M.p. 134°–135° C.; $^1$H NMR: δ9.7–8.3 (br, 1H), 7.56 (AB q, 4H), 3.04 (s, 6H) and 2.26 (s, 3H); $^{13}$C NMR: δ166.48, 154.62, 137.08, 135.28, 129.43, 126.17, 36.70, 11.78 ppm.

Example 4 illustrates the formation of S-(N-acetyl-para-aminophenyl) N,N-dimethylthiocarbamate by the Beckmann rearrangement of the oxime of Example 3, where Ar is 1,4-phenylene and R and R' are methyl.

EXAMPLE 4

The oxime of S-(4'-acetophenyl) N,N-dimethylthiocarbamate (4.76 g, 0.02 mol) was mixed with nitromethane (50 mL) and polyphosphoric acid (0.5 g) was added. The reaction mixture was heated at reflux for 1 h. The flask was cooled to room temperature and dichloromethane (50 mL) added. The organic layer was separated, washed with water, dried over anhydrous magnesium sulfate and concentrated in vacuo to afford S-(N-acetyl-para-aminophenyl)-N,N-dimethylthiocarbamate (4.26 g).

Example 5 illustrates the formation of N-acetyl-para-aminothiophenol by the hydrolysis of S-(N-acetyl-para-aminophenyl)-N,N-dimethylthiocarbamate as shown in equation (III), where Ar is 1,4-phenylene and R and R' are methyl.

EXAMPLE 5

A base solution was prepared by adding potassium hydroxide (1.2 g, 0.02 mol) to ethylene glycol:water (2:1, 15 mL). To the solution was added S-(N-acetyl-para-aminophenyl)-N,N-dimethylthiocarbamate (2.38 g, 0.01 mol). The reaction mixture was heated at reflux for 1.5 h, cooled to room temperature, and extracted with ether (20 mL). Concentration of the organic layer yielded solid (0.4 g) characterized as unreacted starting material. The aqueous layer was carefully acidified to pH 6.0 and extracted with ether (50 mL, 3×). Concentration of this organic layer afforded a solid characterized as N-acetyl-para-aminothiophenol (1.1 g, 66%).

Alternative to the procedures of Examples 3 to 5, N-acetyl-para-aminothiophenol may be produced in accordance with equations (IX), (I) and (II) by hydrolyzing the S-(4'-acetophenyl) N,N-dimethylthiocarbamate produced in Example 2 to 4-acetothiophenol using the procedure of Example 6, forming the oxime of 4-acetothiophenol using the procedure of Example 3, and subjecting such oxime to a Beckmann rearrangement using the procedure of Example 4. Preferably, however, the 4-acetothiophenol may be first acetylated using the procedure of Example 8 hereinafter to form its thioacetate and the latter compound subjected to oxime formation and Beckmann rearrangement in accordance with Examples 3 and 4.

Example 6 illustrates the formation of para-aminothiophenol by the hydrolysis of S-(N-acetyl-para-aminophenyl)-N,N-dimethylthiocarbamate in accordance with equation (IV) where Ar is 1,4-phenylene and R and R' are methyl, under more stringent conditions than are shown in Example 5.

EXAMPLE 6

A base solution is prepared by adding potassium hydroxide (2.24 g, 0.04 mol) to ethylene glycol:water (2:1 15 mL). To the solution is added S-(N-acetyl-para-amino-phenyl)-N,N-dimethylthiocarbamate (2.38 g, 0.01 mL). The reaction mixture is heated at reflux for 3 h, cooled to room temperature and extracted with water (20 mL). The aqueous layer is carefully acidified to pH 6.0 and extracted with ether (50 mL, 3×). Concentration of this organic layer affords a yellow solid characterized as para-aminothiophenol.

Example 7 illustrates the formation of paraaminothiophenol by the further hydrolysis of N-acetyl-paraaminothiophenol, as shown in equation (VI), when Ar is 1,4-phenylene and R is methyl.

EXAMPLE 7

A base solution is prepared by adding potassium hydroxide (2.24 g, 0.04 mol) to ethylene glycol: water (2:1, 15 mL). To the solution is added N-acetyl-para-aminothiophenol (1.7 g, 0.01 mol). The reaction mixture is heated at reflux for 4 h, cooled to room temperature, and extracted with ether (50 mL). The aqueous layer is carefully acidified to pH 6.0 and extracted with ether (50 mL, 3×). Concentration of this organic layer affords a yellow solid characterized as para-aminothiophenol.

Example 8 illustrates the formation of N,S-diacetyl-para-aminothiophenol by the acetylation with acetic anhydride of N-acetyl-para-aminothiophenol, as shown in equation (V), where Ar is 1,4-phenylene, R and R'' are methyl and Y is acetoxy.

EXAMPLE 8

A base solution was prepared by adding potassium hydroxide (1.68 g, 0.03 mol) to methanol (15 mL). Addition of N-acetyl-para-amino-thio-phenol (4.2 g, 0.025 mol) was immediately followed by dropwise addition of acetic anhydride (3.3 g, 0.033 mol). After stirring at room temperature for 15 min, the methanol was removed on a rotary evaporator. The product was precipitated by addition of water (50 mL), collected by filtration, and washed with water. After drying in vacuo (150 mm Hg) at 50° C. overnight, a white crystalline product (4.2 g, 80%) was characterized as N,S-diacetyl-para-aminothiophenol.

Example 9 illustrates the formation of O-(6-acetyl-2-naphthyl) N,N-dimethylthiocarbamate by reaction of 6-hydroxy-2-acetonaphthone with N,N-dimethylthiocarbamoyl chloride (DMTC) in accordance with equation (IX), wherein Ar is 2,6-naphthylene, R and R' are methyl and X is chloride.

EXAMPLE 9

6-Hydroxy-2-acetonaphthone (18.6 g, 0.1 mol) was added to an ice cold solution of potassium hydroxide (6.84 g, 0.12 mol) in methanol (100 mL). The solution was stirred for 0.25 h, N,N-dimethylthiocarbamoyl chloride (14.83 g, 0.12 mol) was added and the reaction mixture was stirred for 0.5 h. Water (150 mL) was added and the solid filtered and washed with water. Drying of the solid in vacuo (150 mm HgA) at 50° C. afforded O-(6-acetyl-2-naphthyl)-N,N-dimethylthiocarbamate (27.3 g, 81.7 % yield). The product was found to be 97.4 % pure by HPLC, $^1$H NMR: $\delta$8.43 (s, 1H), 8.05–7.81 (m, 3H), 7.53 (s, 1H), 7.35–7.27 (m, 1H), 3.47 (s, 3H), 3.39 (s, 3H), and 2.70 (s, 3H); $^{13}$C NMR: $\delta$197.63, 187.34, 135.53, 135.99, 134.39, 130.46, 129.83, 128.07, 124.46, 123.53, 119.48, 43.19, 38.72, and 26.50 ppm.

Example 10 illustrates the formation of S-(6-acetyl-2-naphthyl)-N,N-dimethylthiocarbamate by the pyrolytic rearrangement of O-(6-acetyl-2-naphthyl) N,N-dimethythiocarbamate in accordance with equation (VIII), where Ar is 2,6-naphthylene and R and R' are methyl.

EXAMPLE 10

O-(6-acetyl-2-naphthyl) N,N-dimethylthiocarbamate (10 g, 0.037 mol) was heated at 220° C. for 2 h under an inert atmosphere. After cooling, the reaction product was dissolved in methanol (100 mL) and water (100 mL) was added. A solid precipitated which was collected via filtration, and dried in vacuo (150 mm HgA) at 50° C. to afford the S-(6-acetyl-2-naphthyl) N,N-dimethythiocarbamate (9.6 g, 96% yield). HPLC analysis showed 96% conversion to the product. $^1$H NMR:(CDCl3) $\delta$8.44 (s, 1H), 8.06–7.83 (m, 4H), 7.65–7.60 (m, 1H), 3.09 (br s, 6H) and 2.71 (s, 3H); $^{13}$C NMR: $\delta$197.66, 166.21, 135.49, 135.31, 134.57, 132.97, 132.32, 129.66, 128.35, 124.40, 36.90, and 26.54 ppm.

Example 11 illustrates the formation of the oxime of the sulfur-containing aromatic ketone produced in Example 10, in accordance with equation (I) where Ar is 2,6-naphthylene and R and R' are methyl.

EXAMPLE 11

S-(6-acetyl-2-naphthyl) N,N-dimethylthiocarbamate (6.1 g, 0.025 mol) was added to a solution of hydroxylamine sulfate (8.1 g. 0.05 mol) in ethanol:water (1:2, 25 mL). The reaction mixture was heated to 75° C. and ammonium hydroxide (17M, 2 mL) added. The reaction mixture was heated at reflux for 1 h, water was added, the mixture was cooled and the solid filtered. Drying of the solid in vacuo (150 mm HgA) at 50° C. afforded the oxime of S-(6-acetyl-2-naphthyl) N,N-dimethylthiocarbamate in quantitative yield. Recrystallization with ethanol:water gave a cream colored crystalline solid, m.p. 182°–184° C.; $^1$H NMR:(DMSO-d6) $\delta$11.39 (s, 1H), 8.15 (s, 1H), 8.03–7.91 (s, 4H), 7.49 (d, 1H), 3.36 (s, 6H), and 2.27 (s, 3H); $^{13}$C NMR: $\delta$164.87, 152.64, 135.35, 134.25, 132.80, 132.47, 128.55, 127.53, 126.59, 124.76, 123.60, 36.43, and 11.16 ppm.

Example 12 illustrates the formation of S-(N-acetyl-6-amino-2-naphthyl)-N,N-dimethylthiocarbamate by the Beckmann rearrangement of the oxime produced in Example 11, in accordance with equation (II), where Ar is 2,6-naphthylene and R and R' are methyl.

EXAMPLE 12

The oxime of S-(6-acetyl-2-naphthyl) N,N-dimethylthiocarbamate (1.44 g, 0.005 mol) was mixed with nitromethane (12 mL) and the flask was placed under vacuum (155 mm HgA). Thionyl chloride (0.1 mL) was added and the reaction mixture stirred for 0.25 h. The reaction mixture was heated to reflux under nitrogen for 2 h. The reaction was cooled, diluted with chloroform (50 mL), washed with water (50 mL), dried and concentrated to yield a solid (1.3 g, 90% yield). Liquid chromatographic analysis showed almost complete conversion to the product. $^1$H NMR:(CDCl3) $\delta$8.21 (s, 1H), 7.75–7.1 (m, 5H), 3.01 (s, 6H) and 2.01 (s, 3H); $^{13}$C NMR: $\delta$168.75, 167.98, 136.85, 135.16, 133.67, 132.27, 130.29, 128.20, 123.87, 120.39, 115.77, 37.01, and 24.31 ppm.

Example 13 illustrates the formation of 6-amino-2-thionaphthol by the hydrolysis of S-(N-acetyl-6-amino-2-naphthyl) N,N-dimethylthiocarbamate produced in Example 12, in accordance with equation (IV), where Ar is 2,6-naphthylene and R and R' are methyl.

EXAMPLE 13

S-(N-acetyl-6-amino-2-naphthyl) N,N-dimethylthiocarbamate (2.9 g, 0.01 mol) was mixed with a solution of potassium hydroxide (5.6 g, 0.1 mol) in ethylene glycol:water (9:1, 25 mL). The reaction mixture was heated to reflux for 4 h. The solution was cooled to room temperature and water (100 mL) was added. The aqueous solution was washed with methylene chloride (25 mL), the organic layer was discarded and the aqueous phase was carefully acidified with dilute hydrochloric acid to a pH of 6. A solid precipitated which was collected via filtration and dried in vacuo (150 mm HgA) under nitrogen (1.0 g). The solid was characterized as 6-amino-2-thionaphthol.

Using the procedures of Examples 5, 7, and 8, S-(N-acetyl-6-amino-2-naphthyl) N,N-dimethylthiocarbamate may be hydrolyzed to N-acetyl-6-amino-2-thionaphthol and N-acetyl-6-amino-2-thionaphthol may be acylated to N,S-diacetyl-6-amino-2-thionaphthol, or may be further hydrolyzed to 6-amino-2-thionaphthol, in accordance with equations (III) (V) and (VI).

Using the procedures of Examples 1 to 8 2-hydroxyacetophenone may be converted to S-(N-acetyl-ortho-aminophenyl) N,N-dimethylthiocarbamate, N-acetyl-ortho-aminothiophenol, ortho-aminothiophenol or N,S-diacetyl-ortho-aminothiophenol, in accordance with equation (I) to (X).

We claim:

1. As a new composition of matter, O-(6-acetyl-2-naphthyl)-N,N-dimethylthiocarbamate.

2. As a new composition of matter S-(6-acetyl-2-naphthyl)-N,N-dimethylthiocarbamate.

3. As a new composition of matter, the oxime of S-(4'-acetophenyl) N,N-dimethylthiocarbamate.

4. As a new composition of matter, the oxime of S-(6-acetyl-2-naphthyl) N,N-dimethylthiocarbamate.

5. As a new composition of matter, S-(N-acetyl-6-amino-2-naphthyl) N,N-dimethylthiocarbamate.

6. As a new composition of matter, 6-amino-2-thionaphthol.

* * * * *